United States Patent
Rupprecht et al.

(10) Patent No.: US 6,334,066 B1
(45) Date of Patent: Dec. 25, 2001

(54) METHOD FOR MONITORING GROWTH DISORDER THERAPY

(75) Inventors: Thomas Rupprecht, Uttenreuth; Rainer Kuth, Herzogenaurach, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/467,884

(22) Filed: Dec. 21, 1999

(51) Int. Cl.⁷ ..................................................... A61B 5/055
(52) U.S. Cl. ............................................. 600/411; 128/898
(58) Field of Search .................................... 600/410, 411, 600/416; 128/898; 335/216, 299; 707/102, 103, 104; 378/21

(56) References Cited

U.S. PATENT DOCUMENTS

| | | | |
|---|---|---|---|
| 4,635,643 | * | 1/1987 | Brown .................................. 128/653 |
| 5,247,934 | * | 9/1993 | Wehrli et al. ...................... 128/653.2 |
| 5,270,651 | * | 12/1993 | Wehrli .................................. 324/308 |
| 5,320,102 | * | 6/1994 | Paul et al. ......................... 128/653.2 |
| 5,813,984 | * | 9/1998 | Haaga et al. .......................... 600/410 |

* cited by examiner

Primary Examiner—Marvin M. Lateef
Assistant Examiner—Eleni Mantis Mercader
(74) Attorney, Agent, or Firm—Schiff Hardin & Waite

(57) ABSTRACT

In a method for monitoring growth disorder therapy, a magnetic resonance image of a skeletal body portion, such as a hand, of a candidate for growth disorder therapy is obtained using an open magnetic resonance scanner and using an imaging sequence to produce a tomogram having a slice thickness which approximates the thickness of the hand. The number of visible wrist bones and the width of epiphysis joints in the magnetic resonance image is evaluated to obtain osteo age data, and the osteo age data, in conjunction with an atlas of compiled osteo age data, are used to determine the osteo age of the candidate for growth disorder therapy. The relationship between the osteo age of the candidate and the chronological age of the candidate is used to determine whether growth disorder therapy is required. If growth disorder therapy is administered, such as by administering a hormone, the above procedure is repeated after a predetermined time, and the status of the therapy is again evaluated.

12 Claims, 1 Drawing Sheet

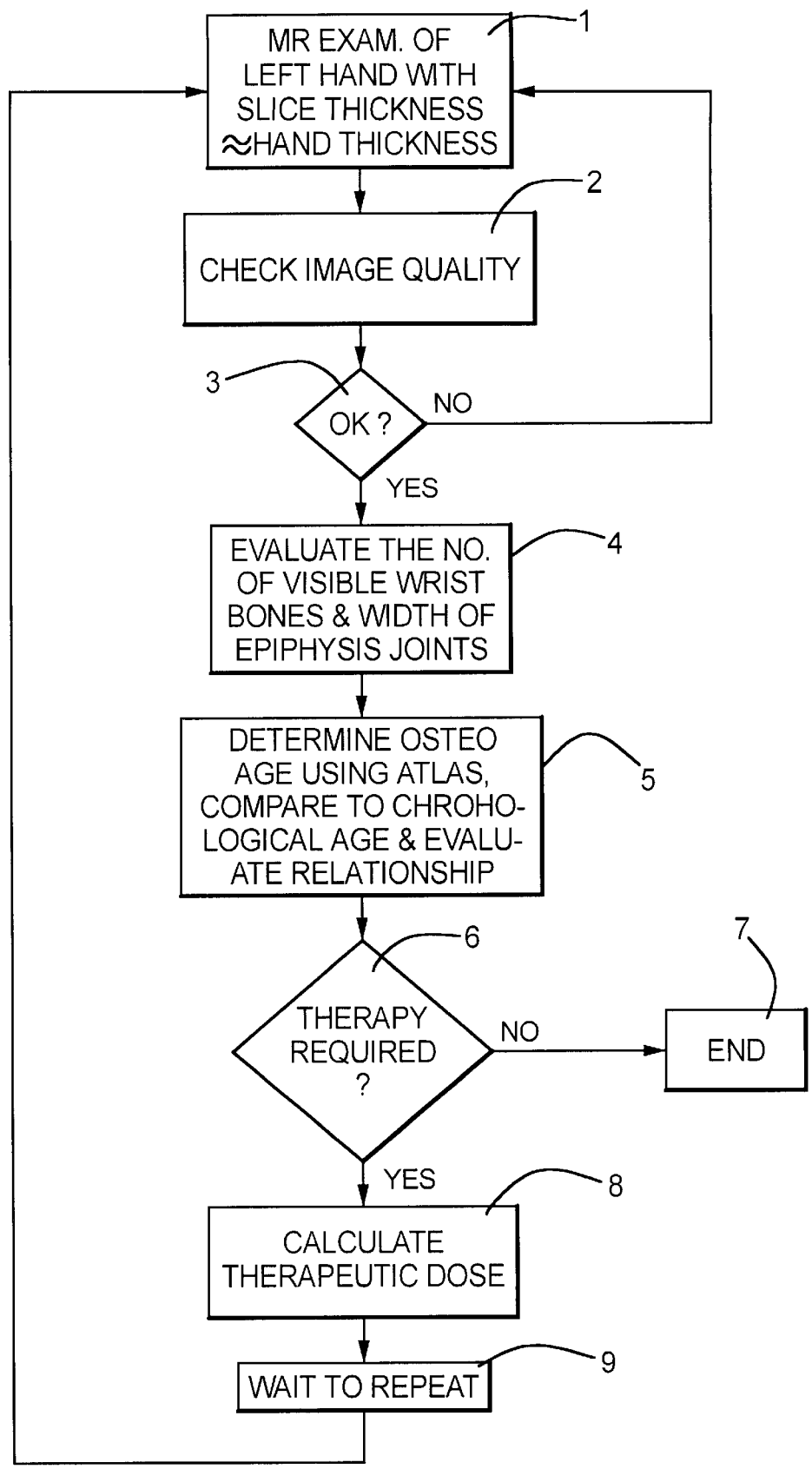

METHOD FOR MONITORING GROWTH DISORDER THERAPY

BACKGROUND OF THE INVENTION

1. Field of the Invention

The present invention is directed to a method for monitoring therapy rendered to treat growth disorders, such as hormone therapy.

2. Description of the Prior Art

In children and young persons, growth disorders can occur due to various defects, for example, due to a pituitary tumor. Such disorders can result in disproportionately short or tall physical height, typically less than 150 cm or greater than 200 cm. Due to the lasting consequences of such anomalous height in adulthood, hormone therapies with which growth can be influenced in juveniles or teens have been employed for some time. Such therapy is complicated and expensive (at least $50,000 to $60,000 per patient). In the context of such therapy, for diagnosis and/or quantitative determination of the growth that still presumably remains, the osteo age of the patients is conventionally determined by frequently repeated x-raying of the wrist bones over the course of years, and analysis of the wrist bones, as seen in the x-ray images, on the basis of an atlas. X-ray examinations of children, however, are generally problematical because the cells have four times the radiation sensitivity of adults (in view of the potential for cancer) and there is no lower threshold for the danger of x-rays.

Heretofore, there had been no methods for avoiding the stress produced by ionizing radiation in the context of monitoring hormone therapy for treating growth disorders.

SUMMARY OF THE INVENTION

It is an object of the present invention to provide a method for monitoring growth disorder therapy wherein repeated x-raying of the therapy subject is minimized, or is entirely foregone.

The above object is achieved in accordance with the principles of the present invention in a method for monitoring growth disorder therapy wherein repeated images of the skeleton of the hand of a therapy subject are produced in a magnetic resonance (MR) tomography apparatus. The osteo age of the patient is then identified from the magnetic resonance images, and is placed in relationship with the chronological age on the basis of known maturation stages, by comparing the size and the number of visible wrist bones in the images, as well as the width of the growth joints (epiphysis joints). A determination as to whether therapy is required and, if so, a calculation of the therapeutic hormone dose, are then undertaken. After a suitable time, such as the passage of approximately six months, another MR image is obtained and the analysis and evaluation are repeated.

Magnetic resonance scanners have been known for some time, however, conventionally the osteo age of a subject has not been determined on the basis of images obtained with such MR scanners, because the examination conducted in such an MR scanner is expensive, due to the high apparatus price, and the examination has heretofore been considered overly complicated, due to the need for accurate positioning, and the necessary care, particularly for young patients, in the confined examination tube (chamber) of a conventional MR scanner. Moreover, such examinations typically require measuring times of several minutes using conventional measuring sequences.

These disadvantages do not exist in the inventive method, even though MR scanning is employed, because the aforementioned MR images of the wrist bone are acquired under conditions that are completely different from conventional MR imaging and are an integral part of the overall therapeutic procedure.

The MR images which are acquired in accordance with the invention are obtained in a type of MR scanner known as an open scanner. This type of MR scanner has a lateral axis for the patient, thereby making patient fear and claustrophobic concerns much lower, and greatly facilitating positioning within the MR scanner. Such open MR scanners, for example, have magnetic pole pieces disposed parallel to each other connected by a C-shaped yoke or connecting element and are commercially available from a number of sources.

DESCRIPTION OF THE DRAWINGS

The single FIGURE is a flowchart of a method for monitoring growth disorder therapy in accordance with the principles of the present invention.

DESCRIPTION OF THE PREFERRED EMBODIMENTS

As indicated in step 1 of the flowchart in the FIGURE, the inventive method for monitoring growth disorder therapy begins with a magnetic resonance examination of a hand, such as the left hand, of a therapy subject or therapy candidate. A scanning sequence is used for producing an image of a slice thickness which approximately corresponds to the thickness of the hand being scanned. This MR image is produced using an open MR scanner, for example, a scanner which is commercially available from Siemens AG known as the Magnetom OPEN. By using an open scanner, the patient fear and claustrophobic concerns which are sometimes associated with a tunnel or tube type MR scanner are avoided. These concerns may be particularly exaggerated in the case of younger patients, and since many candidates for hormone therapy of this type fall into the age group for which scanning using a closed MR scanner is particularly problematic, the use of an open MR scanner greatly facilitates the repeated scannings which are necessary during the course of hormone therapy monitoring. The use of an MR scanner has the additional advantage of avoiding exposure of young patients to ionizing radiation, in view of the particular susceptibility which young patients have to complications resulting from over-exposure to x-rays. For the purpose of obtaining the MR image in accordance with the invention, the patient is placed directly in front of the open MR scanner on a chair, such as an MR-compatible kneeler. Such a kneeler is provided in the Procedure Package for the aforementioned Magnetom OPEN scanner. The patient extends the hand to be examined between the pole pieces of the magnet, into the region known as the measuring volume, wherein excitation and readout of MR signals is possible.

Fast measuring sequences, for example, the TrueFisp sequence, are employed for conducting the MR measurement. Obtaining a relatively thick tomogram, wherein all of the wrist bones lie in the same plane, is advantageous. The measuring times are typically in the range of 1 second.

Moreover, since there is no radiation exposure involved, a parent of a younger examination subject, for example, can hold the hand immobile during the examination within the measuring volume. If blurring of the image nevertheless occurs, the scan can be immediately repeated without risk or injury. Moreover, due to the absence of an ionizing radiation load and the low costs associated with this type of MR scan, the examination can be repeated relatively often in order to monitor the therapy in a very precise manner.

As also shown in the flowchart in the FIGURE, in step 2 the image quality is checked and, as noted above, a determination is then made in step 3 as to whether the scan should be repeated. If the image quality is acceptable, the method proceeds to step 4, wherein the number of visible bones and the width of the epiphysis joints are evaluated (identified).

Using an atlas of the type which is conventionally compiled for other purposes and which is readily available to those of ordinary skill in the art, the data obtained in step 4 are used in step 5 to determine the osteo age of the subject, i.e., the age of the subject as represented by the data collected in step 4. This osteo age is then compared to the chronological age and the relationship between the osteo age and the chronological age is evaluated.

Based on this evaluation, in step 6 a determination is made as to whether therapy is required. If not, the procedure ends at step 7.

If therapy is required, a calculation is then made in step 8 as to the appropriate therapeutic hormonal dose, and this is administered to the subject. After an appropriate waiting time, in step 9, the therapy subject returns to the clinic, hospital or physician's office, and the above-described evaluation procedure is repeated and the therapy is modified, if necessary. An appropriate waiting period in step 9 may be, for example, approximately six months.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for monitoring growth disorder therapy comprising the steps of:
   obtaining an image by magnetic resonance scanning of a skeletal body portion of a candidate for growth disorder therapy, said image containing osteo age indicators;
   evaluating said osteo age indicators in said magnetic resonance image to obtain osteo age data;
   identifying an osteo age of said candidate for growth disorder therapy from said osteo age data using an atlas of compiled osteo age data;
   determining a relationship between the osteo age of the candidate for growth disorder therapy and the chronological age of the candidate for growth disorder therapy; and
   dependent on said relationship, determining whether growth disorder therapy is required for said candidate for growth disorder therapy.

2. A method as claimed in claim 1 wherein the step of obtaining a magnetic resonance image comprises obtaining said magnetic resonance image using an open magnetic resonance scanner.

3. A method as claimed in claim 1 wherein the step of obtaining a magnetic resonance image comprises obtaining said magnetic resonance image with a slice thickness which is substantially equal to a thickness of said skeletal body part.

4. A method as claimed in claim 1 wherein the step of obtaining a magnetic resonance image comprises obtaining a magnetic resonance image of a hand of said candidate for growth disorder therapy.

5. A method as claimed in claim 1 wherein the step of evaluating said osteo age indicators comprise evaluating a number of bones and a width of epiphysis joints in said skeletal body portion.

6. A method as claimed in claim 1 comprising the additional step of administering a hormone to said candidate for growth disorder therapy as a part of said therapy.

7. A method as claimed in claim 6 comprising the additional step of waiting a time after administration of said hormone and obtaining an updated magnetic resonance image of said skeletal body portion, evaluating osteo age indicators in said updated magnetic resonance image to obtain updated osteo age data, determining the osteo age of said candidate for growth disorder therapy at a time of said updated magnetic resonance image using said updated osteo age data and said atlas, determining an updated relationship between the osteo age of said candidate for growth disorder therapy at said time of said updated magnetic resonance image and the chronological age of said candidate for growth disorder therapy at said time of said updated magnetic resonance image, and determining whether said therapy requires modification dependent on said updated relationship.

8. A method as claimed in claim in claim 7 wherein the step of waiting a time comprises waiting approximately six months after administering said hormone to obtain said updated magnetic resonance image.

9. A method as claimed in claim 8 comprising the additional step of administering a hormone to said candidate for growth disorder therapy as a part of said therapy.

10. A method as claimed in claim 9 wherein said time after administering said hormone comprises approximately six months.

11. A method for monitoring growth disorder therapy comprising the steps of:
    obtaining a magnetic resonance image of a hand of a candidate for growth disorder therapy using an open magnetic resonance scanner and an imaging sequence to obtain a tomogram with a slice thickness approximating a thickness of said hand, said magnetic resonance image containing visible wrist bones and epiphysis joints;
    evaluating a number of said visible wrist bones and a width of said epiphysis joints to obtain osteo age data;
    determining an osteo age of said candidate for growth disorder therapy from an atlas of complied osteo age data using said osteo age data obtained by evaluating said magnetic resonance image;
    determining a relationship between said osteo age of said candidate for growth disorder therapy and the chronological age of said candidate for growth disorder therapy; and
    from said relationship, determining whether growth disorder therapy is required for said candidate for growth disorder therapy.

12. A method as claimed in claim 11 comprising the additional steps of:
    waiting a time after administering said hormone and at said time obtaining an updated magnetic resonance image of said hand using an open magnetic resonance scanner and using an imaging sequence to obtain a tomogram having a slice thickness substantially equal to said thickness of said hand, said update magnetic resonance image also containing visible wrist bones and epiphysis joints;
    evaluating a number of said visible wrist bones and a width of said epiphysis joints in said updated magnetic resonance image to obtain updated osteo age data;

determining the osteo age of said candidate for growth disorder therapy at said time of said updated magnetic resonance image using said atlas and said update osteo age data;

determining an updated relationship between said osteo age of said candidate for growth disorder therapy at said time of said updated magnetic resonance image and the chronological age of said candidate for growth disorder therapy at said time of said updated magnetic resonance image; and dependent on said updated relationship, determining whether said therapy requires modification.

* * * * *